(12) United States Patent
Okawa

(10) Patent No.: US 10,494,748 B2
(45) Date of Patent: Dec. 3, 2019

(54) THERMAL BOND NON-WOVEN FABRIC CONTAINING CYCLIC OLEFIN RESIN

(71) Applicant: Polyplastics Co., Ltd., Tokyo (JP)

(72) Inventor: Hidetoshi Okawa, Tokyo (JP)

(73) Assignee: Polyplastics Co., Ltd., Tokyo (JP)

( * ) Notice: Subject to any disclaimer, the term of this patent is extended or adjusted under 35 U.S.C. 154(b) by 12 days.

(21) Appl. No.: 15/567,710

(22) PCT Filed: May 10, 2016

(86) PCT No.: PCT/JP2016/063851
§ 371 (c)(1),
(2) Date: Oct. 19, 2017

(87) PCT Pub. No.: WO2016/194553
PCT Pub. Date: Dec. 8, 2016

(65) Prior Publication Data
US 2018/0105964 A1    Apr. 19, 2018

(30) Foreign Application Priority Data
Jun. 3, 2015 (JP) .................................. 2015-113261

(51) Int. Cl.
| | | |
|---|---|---|
| *D04H 1/4291* | (2012.01) | |
| *D04H 1/4382* | (2012.01) | |
| *D04H 1/541* | (2012.01) | |
| *D04H 3/153* | (2012.01) | |
| *A61K 9/70* | (2006.01) | |
| *D01F 6/30* | (2006.01) | |
| *D04H 3/16* | (2006.01) | |
| *A61K 47/32* | (2006.01) | |

(52) U.S. Cl.
CPC ............. *D04H 1/4291* (2013.01); *A61K 9/70* (2013.01); *A61K 47/32* (2013.01); *D01F 6/30* (2013.01); *D04H 1/4382* (2013.01); *D04H 1/541* (2013.01); *D04H 3/153* (2013.01); *D04H 3/16* (2013.01); *D10B 2321/02* (2013.01); *D10B 2401/041* (2013.01); *D10B 2509/00* (2013.01)

(58) Field of Classification Search
CPC ...... A61K 9/70; A61K 47/32; D10B 2509/00; D10B 2321/02; D04H 1/4291; D04H 3/16; D04H 1/10; D04H 1/12; D04H 1/541; D01F 6/30; C08L 2205/025; Y10T 442/697; Y10T 442/692; Y10T 442/684; Y10T 442/615; Y10T 442/313; Y10T 428/24942; B32B 2262/14; B32B 5/08
USPC ....... 442/330, 274, 310, 341, 361, 403, 411, 442/415
See application file for complete search history.

(56) References Cited

U.S. PATENT DOCUMENTS

| | | | |
|---|---|---|---|
| 6,657,033 B1 * | 12/2003 | Sartori | B32B 27/12 526/348.1 |
| 6,927,184 B1 * | 8/2005 | Jacobs-Hartwig | B01D 39/1623 442/400 |
| 8,895,668 B2 | 11/2014 | Nakane et al. | |
| 2010/0105273 A1 * | 4/2010 | Motomura | B32B 5/022 442/329 |
| 2010/0225032 A1 * | 9/2010 | Nakane | B29C 49/0005 264/537 |
| 2011/0212660 A1 * | 9/2011 | Okawa | D01D 5/0038 442/351 |
| 2014/0308868 A1 | 10/2014 | Nambiar et al. | |
| 2016/0329038 A1 * | 11/2016 | Watanabe | B60R 13/08 |

FOREIGN PATENT DOCUMENTS

| | | | |
|---|---|---|---|
| CN | 1313915 A | 9/2001 | |
| CN | 101835842 A | 9/2010 | |
| EP | 1198629 B1 | 6/2006 | |
| JP | H08-144165 | 6/1996 | |
| JP | 2000-265330 A | 9/2000 | |
| JP | 2003-504523 A | 2/2003 | |
| JP | 2013-049943 A | 3/2013 | |
| JP | 2014-148774 A | 8/2014 | |
| WO | WO 2006/3471 A1 | 10/2000 | |
| WO | WO 2011/158644 A1 | 12/2011 | |
| WO | WO-2015097885 A1 * | 7/2015 | ............. B60R 13/08 |

OTHER PUBLICATIONS

Millipore Sigma website, Thermal Transitions of Homopolymers; Glass Transition & Melting Point, https://www.sigmaaldrich.com/technical-documents/articles/materials-science/polymer-science/thermal-transitions-of-homopolymers.html (Year: 2019).*

(Continued)

*Primary Examiner* — Jennifer A Steele
(74) *Attorney, Agent, or Firm* — Knobbe, Martens, Olson & Bear, LLP

(57) ABSTRACT

A non-woven fabric that absorbs only a small amount of volatile low molecular weight compound, and that has good texture when used as a non-woven fabric that makes contact with human skin. This thermal bond non-woven fabric containing cyclic olefin resin includes at least: fibers (A) containing at least 50 mass % of a cyclic olefin resin (A1) having a glass transition temperature $Tg_{A1}$° C.; and fibers (B) containing at least 10 mass % of either a cyclic olefin resin (B1) having a glass transition temperature $Tg_{B1}$° C., or a crystalline thermoplastic resin (B2) having a melting point $Mp_{B2}$° C.; the fibers (A) and the fibers (B) being heat-spliced together; wherein $Tg_{A1} > Tg_{B1}$ or $Tg_{A1} > Mp_{B2}$, and either the difference between the glass transition temperature $Tg_{A1}$° C. and the glass transition temperature $TgB1$° C. or the difference between the glass transition temperature $Tg_{A1}$° C. and the melting point $Mp_{B2}$° C. exceeds 20° C.

6 Claims, No Drawings

(56) References Cited

OTHER PUBLICATIONS

Extended Search Report in European Patent Application No. 16802990.8, dated Mar. 27, 2018.
Office Action issued in Chinese Patent Application No. 201680030476.7, dated Aug. 6, 2018.

* cited by examiner

THERMAL BOND NON-WOVEN FABRIC CONTAINING CYCLIC OLEFIN RESIN

RELATED APPLICATIONS

This application is the U.S. National Phase under 35 U.S.C. § 371 of International Application PCT/JP2016/063851, filed May 10, 2016, designating the U.S., and published in Japanese as WO 2016/194553 on Dec. 8, 2016, which claims priority to Japanese Patent Application No. 2015-113261, filed Jun. 3, 2015, the entire contents of which are incorporated herein by reference.

TECHNICAL FIELD

The present invention relates to a thermal bond non-woven fabric containing a cyclic olefin-based resin, which can be used, for example, for a patch or the like.

BACKGROUND ART

Non-woven fabrics are used in a wide range of fields such as medical materials such as masks, patches and the like, interior materials of automobiles such as ceiling materials, seats, and the like, agricultural materials, construction materials, civil engineering materials, in addition to battery separators, potable water filters, manufacturing filters, and the like.

Non-woven fabrics are produced by first forming a mass of long fibers or short fibers called a web, and next, bonding between the fibers. As a method of bonding between the fibers, a method of bonding between the fibers by melting by heating a part of the fibers is known. As such a method of producing a non-woven fabric by utilizing heating, for example, a thermal bond method, a melt-blown method, a spun-bond method and the like are known.

Investigation of thermoplastic resins constituting the web of fibers for producing non-woven fabrics is being carried out. For example, non-woven fabrics where the web of fibers is a composite fiber consisting of resins having differing melting points or glass transition points have been disclosed (Patent Documents 1 and 2).

Patent Document 1: Japanese Unexamined Patent Application, Publication No. 2013-049943

Patent Document 2: Japanese Unexamined Patent Application, Publication No. 2014-148774

DISCLOSURE OF THE INVENTION

Problems to be Solved by the Invention

Incidentally, the physical properties required of non-woven fabrics differ according to the application. For example, in the case of a composite fiber non-woven fabric used for a patch material, it is one which is mainly used on human skin, and therefore, it is required that it not have an uncomfortable feeling of an adhesion sensation (i.e. it should have a good feel). Further, non-woven fabrics having extremely low absorbency of medicaments are required. Further, a patch should exert its effect by allowing a long-term medication to permeate the skin. This effect cannot be exerted for the portion of the medication which is absorbed in the non-woven fabric of the patch. Therefore, as a material used for a non-woven fabric for a patch, in some cases there is demand for using one which has a low absorbance of volatile low molecular compounds such as medications and the like.

On the other hand, as methods of producing non-woven fabrics, for example, web forming methods such as a dry method, wet method, spun-bond method, melt-blown method, air-laid method and the like, and production methods using fiber bonding methods of a web such as a chemical bond (immersion) method, chemical bond (spray) method, needle punch method, spun lace method, thermal bond method, and the like, may be mentioned.

In the case of producing a non-woven fabric using a thermal bond method, for example, it is possible to produce a non-woven fabric consisting of two or more types of thermoplastic fibers with differing heat resistances, by bonding by thermal fusion between one fibers having the higher heat resistance the other fiber having the lower heat resistance. In this case, it is possible to obtain a bond by thermal bonding at a temperature where the thermoplastic fiber with the lower heat resistance melts, but the other fiber having the higher heat resistance does not melt. A non-woven fabric produced from two or more types of thermoplastic fiber having differing heat resistances can be produced by adjusting the type of the thermoplastic fibers or the thermal fusion temperature.

As a thermoplastic fiber (which hereafter may also be referred to as thermal bond fiber) for producing a non-woven fabric using such a thermal bond method, for example, a core-shell type composite spin with a polypropylene resin as the core, and a high-density polyethylene resin as the shell may be mentioned. Such a core-shell type composite spin is used in particular as a thermal bond fiber for general purpose non-woven fabric articles such as for sanitary applications and the like. As a thermal bond fiber which can be used, other than the above described polypropylene/high density polyethylene core-shell type composite spin, a thermal bond fiber of 100% high density polyethylene, or a thermal bond fiber of a low melting point polyester may be mentioned. For example, in the case of a polyester wet process non-woven fabric, it is possible to produce a non-woven fabric using a thermal bond fiber consisting of a polyethylene terephthalate fiber having a high heat resistance, and a low melting point polyester fiber having a low heat resistance.

However, these previously used thermal bond non-woven fabrics have a high rate of absorption of volatile low molecular compounds, or cannot be said to have a good feel.

The present invention is one made in order to solve the above described problems, and the objective thereof is to provide a non-woven fabric having a low absorptivity with respect to volatile low molecular compounds, which also has a good feel in the case that the non-woven fabric is used in contact with human skin.

Means for Solving the Problems

The present inventors carried out repeated diligent research in order to solve the above described problems. As a result, they discovered that the above described problem can be solved by making the fibers used for the non-woven fabric a cyclic olefin-based resin-containing thermal bond non-woven fabric wherein a fiber (A) comprising a predetermined amount of a cyclic olefin-based resin (A1), and a fiber (B) comprising a cyclic olefin-based resin (B1) or a crystalline thermoplastic resin (B2) are thermally fused, and thus completed the present invention. More specifically, the present invention provides the following.

The first aspect of the invention is a cyclic olefin-based resin-containing thermal bond non-woven fabric comprising at least a fiber (A) comprising no less than 50 mass % of a cyclic olefin-based resin (A1) with a glass transition point $Tg_{A1}$° C., and a fiber (B) comprising no less than 10 mass % of a cyclic olefin-based resin (B1) having a glass transition point $Tg_{B1}$° C., or a crystalline thermoplastic resin (B2) having a melting point $Mp_{B2}$° C., wherein the fiber (A) and the fiber (B) are thermally fused, and wherein $Tg_{A1} > Tg_{B1}$, or $Tg_{A1} > Mp_{B2}$, and wherein a difference between the glass transition point $Tg_{A1}$° C. and the glass transition point $Tg_{B1}$° C., or a difference between the glass transition point $Tg_{A1}$° C. and the melting point $Mp_{B2}$° C., exceeds 20° C.

The second aspect of the invention is a cyclic olefin-based resin-containing thermal bond non-woven fabric according to the first aspect wherein the fiber (B) comprises no less than 10 mass % of the cyclic olefin-based resin (B1) having the glass transition point $Tg_{B1}$° C.

The third aspect of the invention is a cyclic olefin-based resin-containing thermal bond non-woven fabric according to the first or second aspect wherein the fiber (A) and the fiber (B) are short fibers having a length of 0.2 mm to 10 mm.

The fourth aspect of the invention is a cyclic olefin-based resin-containing thermal bond non-woven fabric according to any one of the first to third aspects, formed by a wet method.

The fifth aspect of the invention is a cyclic olefin-based resin-containing thermal bond non-woven fabric according to any one of the first to fourth aspects wherein the cyclic olefin-based resin-containing thermal bond non-woven fabric is a substrate for a patch.

Effects of the Invention

The cyclic olefin-based resin-containing thermal bond non-woven fabric of the present invention is a non-woven fabric with a low absorptivity with respect to volatile low molecular compounds, which has a good feel in the case that the non-woven fabric is used in contact with human skin.

PREFERRED MODE FOR CARRYING OUT THE INVENTION

Below, one embodiment of the cyclic olefin-based resin-containing thermal bond non-woven fabric of the present invention is explained in detail. The present invention is not limited by the below embodiment, and may be implemented with the addition of suitable modifications within a scope which achieves the objective of the present invention.

<Cyclic Olefin-Based Resin-Containing Thermal Bond Non-Woven Fabric>

The cyclic olefin-based resin-containing thermal bond non-woven fabric of the embodiment of the present invention is a cyclic olefin-based resin-containing thermal bond non-woven fabric comprising at least a fiber (A) comprising no less than 50 mass %, preferably no less than 70 mass %, and particularly preferably no less than 90 mass % of a cyclic olefin-based resin (A1) having a glass transition point $Tg_{A1}$° C., and a fiber (B) comprising no less than 10 mass %, preferably no less than 20 mass %, and particularly preferably no less than 30 mass % of a cyclic olefin-based resin (B1) having a glass transition point $Tg_{B1}$° C., or a crystalline thermoplastic resin (B2) having a melting point $Mp_{B2}$° C. By using the fiber (A) comprising no less than 50 mass % of the cyclic olefin-based resin (A1), it is possible to make a non-woven fabric having a low rate of absorption of volatile low molecular compounds. Further, at the same time, it is possible to provide a good feel of the non-woven fabric with respect to human skin. Therefore, this is especially useful as a non-woven fabric for use as a patch, which is adhered to human skin and which requires a low absorptivity with respect to volatile low molecular compounds.

Further, the relationship between the glass transition point $Tg_{A1}$° C. of the cyclic olefin-based resin (A1) included in the fiber (A), and the glass transition point $Tg_{B1}$° C. of the cyclic olefin-based resin (B1) included in the fiber (B), or the melting point $Mp_{B2}$° C. of the crystalline thermoplastic resin (B2) is as follows.

Namely, $Tg_{A1} > Tg_{B1}$, or $Tg_{A1}$° C. $> Mp_{B2}$, and the difference between the glass transition point $Tg_{A1}$° C. and the glass transition point $Tg_{B1}$° C., or the difference between the glass transition point $Tg_{A1}$° C. and the melting point $Mp_{B2}$° C., exceeds 20° C. By setting $Tg_{A1}$, $Tg_{B1}$, and $Mp_{B2}$ within such a range, it is possible to produce a cyclic olefin-based resin-containing thermal bond non-woven fabric by thermal fusion.

Below, the cyclic olefin-based resin which may be included in the fiber (A) and the fiber (B) is explained.

[Cyclic Olefin-Based Resin]

The cyclic olefin-based resin in the embodiment of the present invention is included in the fiber (A) of the embodiment of the present invention. Further, it may be included in the fiber (B) of the embodiment of the present invention. The cyclic olefin-based resin is a resin comprising a cyclic olefin component as a polymerization component. For example, an addition polymer of a cyclic olefin, or a hydrogenated product thereof, or a copolymer of a cyclic olefin and an α-olefin, or a hydrogenated product thereof may be mentioned. The cyclic olefin-based resin may be used as one single type, or two or more types thereof may be used in combination. Cyclic olefin-based resins have an extremely low absorptivity with respect to volatile low molecular compounds. Therefore, it can be used with especial usefulness, for example, as a substrate for a patch having a content comprising a volatile low molecular compound. Further, "volatile low molecular compound" means a volatile low molecular compound with a molecular weight of no more than 800, preferably no more than 500, and for example, dl-camphor, l-menthol, methyl salicylate, tulobuterol, nicotine, bromhexine hydrochloride, and the like may be mentioned.

As the cyclic olefin-based resin, one where, in the above described polymer or the above described copolymer comprising in the main chain structural units derived from a cyclic olefin, an unsaturated compound further having a polar group is grafted or copolymerized, may also be mentioned.

As the polar group, for example, a carboxyl group, acid anhydride group, epoxy group, amide group, ester group, hydroxyl group, and the like may be mentioned, and as the unsaturated compound having a polar group, (meth)acrylic acid, maleic acid, maleic anhydride, itaconic anhydride, glycidyl (meth)acrylate, alkyl (meth)acrylate (carbon number 1 to 10) esters, alkyl maleate (carbon number 1 to 10) esters, (meth)acrylamide, (meth)acrylic acid-2-hydroxyethyl, and the like may be mentioned.

Further, as a copolymer which may be used for the cyclic olefin-based resin in the embodiment of the present invention, commercially available resins may be used. As the commercially available cyclic olefin-based resins, for example, TOPAS (registered trademark; produced by TOPAS Advanced Polymers), APEL (registered trademark; produced by Mitsui Chemicals, Inc.), ZEONEX (registered trademark; produced by Zeon Corporation), ZEONOR (registered trademark; produced by Zeon Corporation), ARTON (registered trademark, produced by JSR Corporation), and the like may be mentioned.

As an addition copolymer of a cyclic olefin and an α-olefin, as a particularly preferable example, a copolymer comprising [1] a structural unit derived from an α-olefin with a carbon number of 2 to 20, and [2] a structural unit derived from a cyclic olefin represented by the below general formula (b), may be mentioned.

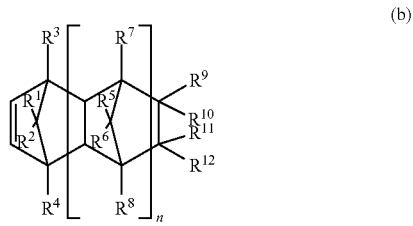
(b)

(In the formula, $R^1$ to $R^{12}$ may be the same or different, and are selected from the group consisting of a hydrogen atom, a halogen atom, and a hydrocarbon group, $R^9$ and $R^{10}$, and $R^{11}$ and $R^{12}$ may be integrated to form a divalent hydrocarbon group, $R^9$ and $R^{10}$, and $R^{11}$ and $R^{12}$ may form a ring with each other. Further, n represents 0 or a positive integer, and in the case that n is 2 or more, among the respective repeating units, $R^5$ to $R^9$ may respectively be the same or different.)

[[1] α-olefin With a Carbon Number of 2 to 20]

The α-olefin with a carbon number of 2 to 20 is not particularly limited. For example, the same one as disclosed in Japanese Unexamined Patent Application, First Publication No. 2007-302722 may be mentioned. Further, this α-olefin may be used as one single type, or two or more types may be used at the same time. Among these, the single use of ethylene is most preferable.

[[2] Cyclic Olefin Represented by General Formula (b)]

The cyclic olefin represented by the general formula (b) is explained. $R^1$ to $R^{12}$ in the general formula (b) may respectively be the same or different, and are selected from the group consisting of a hydrogen atom, a halogen atom, and a hydrocarbon group. As a specific example of the cyclic olefin represented by the general formula (b), the same as those disclosed in Japanese Unexamined Patent Application, First Publication No. 2007-302722 may be mentioned.

These cyclic olefins may be used as one single type, or two or more types may be used in combination. Among these, the single use of bicyclo[2.2.1]hepta-2-ene (common name: norbornene) is preferable.

The polymerization method of the [1] α-olefin with a carbon number of 2 to 20 and [2] the cyclic olefin represented by the general formula (b), and hydrogenation method of the obtained polymer are not particularly limited, and may be carried out by a publicly known method.

Further, the used polymerization catalyst is not particularly limited, and the cyclic olefin-based resin may be obtained by a publicly known method using a previously known catalyst such as a Ziegler-Natta-based, metathesis-based, metallocene-based catalyst the like.

Further, the hydrogenation method of the obtained cyclic olefin-based resin is not particularly limited, and a previously known method may be applied.

Further, the cyclic olefin-based resin may also include other copolymerizable unsaturated monomer components as required, within a range which does not impair the objective of the present invention, in addition to the [1] α-olefin component with a carbon number of 2 to 20, and [2] cyclic olefin component represented by the general formula (b). An unsaturated monomer which may be optionally copolymerized is not particularly limited, and for example, a hydrocarbon-based monomer including two or more carbon-carbon double bonds in one molecule may be mentioned. As specific examples of the hydrocarbon-based monomer including two or more carbon-carbon double bonds in one molecule, the same as those in Japanese Unexamined Patent Application, First Publication No. 2007-302722 may be mentioned.

Among cyclic olefin-based resins, addition copolymers of ethylene and norbornene have a low absorptivity of volatile low molecular compounds, and therefore are especially favorable. Accordingly, as the cyclic olefin-based resin in the embodiment of the present invention, addition copolymers of ethylene and norbornene are especially preferable.

The glass transition point of the cyclic olefin-based resin is preferably 50° C. to 190° C., more preferably 60° C. to 190° C., and even more preferably 70° C. to 190° C. By making the glass transition point of the cyclic olefin-based resin 50° C. or more, a non-woven fabric with a preferable heat resistance can be obtained. By making the glass transition point of the cyclic olefin-based resin 190° C. or less, it is possible to ensure the good spinnability required for a melt-spinning process.

The glass transition point (Tg) of the cyclic olefin-based resin is taken as the value measured by the DSC method (the method disclosed in JIS K7121) under conditions of a temperature increase rate of 10° C./min.

The cyclic olefin-based resin preferably has an MVR of 1 ml/10 min to 100 ml/10 min, measured under conditions of 260° C., and a load of 2.16 kg, by a method in conformance with ISO1133. If the MVR of the cyclic olefin-based resin is less than 1 ml/10 min, the flowability may be impaired in some cases. Further, if the MVR of the cyclic olefin-based resin becomes higher than 100 ml/10 min, the mechanical strength of the cyclic olefin-based resin itself decreases, and it may become unsuitable for non-woven fabric applications in some cases.

(Other Components)

In the fiber (A) of the embodiment of the present invention, components other than the cyclic olefin-based resin may also be included. In the fiber (B) of the embodiment of the present invention, components other than the cyclic olefin-based resin or crystalline thermoplastic resin may also be included. As such other components, other types of thermoplastic resins, or additives such as stabilizers, toughening agents, plasticizers, colorants and the like are mentioned as examples.

[Crystalline Thermoplastic Resin]

The crystalline thermoplastic resin in the embodiment of the present invention is not particularly limited provided that it is a previously known crystalline thermoplastic resin. For example, resins such as polyethylene terephthalate resin, nylon resin, polypropylene resin, polyethylene resin and the like may be mentioned.

[Cyclic Olefin-Based Resin-Containing Thermal Bond Non-Woven Fabric]

The cyclic olefin-based resin-containing thermal bond non-woven fabric of the embodiment of the present invention is formed by thermally fusing a fiber (A) comprising no less than 50 mass %, preferably no less than 70 mass %, and particularly preferably no less than 90 mass % of a cyclic olefin-based resin (A1), and a fiber (B) comprising no less than 10 mass %, preferably no less than 20 mass %, more preferably no less than 30 mass %, and particularly preferably no less than 40 mass % of a cyclic olefin-based resin (B1) having a glass transition point $Tg_{B1}$° C., or a crystalline thermoplastic resin having a melting point $Mp_{B2}$° C.

In the fiber (B), the fiber comprising no less than 10 mass % resin may be a fiber consisting of a single component of a cyclic olefin-based resin (B1) or a crystalline thermoplastic resin (B2) having a melting point $Mp_{B2}$° C., or may be a blended resin where a plurality of resin components are blended. Or fiber may be a fiber consisting of a core-shell type composite spin, where the resin of the shell portion of the core-shell type composite spin is used as the cyclic olefin-based resin (B1) or a crystalline thermoplastic resin (B2) component having a melting point $Mp_{B2}$° C., as a resin comprised as no less than 10 mass % of the component (B1) or (B2) among all of the core-shell type composite spin.

Further, the glass transition point $Tg_{A1}$° C. of the cyclic olefin-based resin (A1) included in the fiber (A), and the glass transition point $Tg_{B1}$° C. of the cyclic olefin-based resin (B1), or the melting point $Mp_{B2}$° C. of the crystalline thermoplastic resin (B2) included in the fiber (B), have the following relationship.

$Tg_{A1} > Tg_{B1}$, or $Tg_{A1}$° C. $> Mp_{B2}$, and the difference between the glass transition point $Tg_{A1}$° C. and the glass transition point $Tg_{B1}$° C., or the difference between the glass transition point $Tg_{A1}$° C. and the melting point $Mp_{B2}$° C. exceeds 20° C. By blending two types of fiber having different heat resistances, and melting the fiber having the lower heat resistance by heating, it becomes possible to thermally fuse the fibers to each other. By making $Tg_{A1}$, $Tg_{B1}$, and $Mp_{B2}$ within this range, it is possible to produce a cyclic olefin-based resin-containing thermal bond non-woven fabric by thermal fusion.

Namely, in the case of including no less than 10 mass % of the cyclic olefin-based resin (B1) in the fiber (B), the difference between the glass transition point $Tg_{A1}$ of the cyclic olefin-based resin (A1) included in the fiber (A) and the glass transition point $Tg_{B1}$ of the cyclic olefin-based resin (B1) included in the fiber (B) exceeds 20° C. In the case of including no less than 10 mass % of the crystalline thermoplastic resin (B2) in the fiber (B), the difference between the glass transition point $Tg_{A1}$ of the cyclic olefin-based resin (A1) included in the fiber (A) and the melting point $Mp_{B2}$ of the crystalline thermoplastic resin (B2) included in the fiber (B) exceeds 20° C. In the case that the difference between the glass transition point $Tg_{A1}$° C. and the glass transition point $Tg_{B1}$° C., or the difference between the glass transition point $Tg_{A1}$° C. and the melting point $Mp_{B2}$° C. is no greater than 20° C., in the processing for forming the non-woven fabric, it is not possible to form the non-woven fabric into a sheet.

By including such a fiber (A) and fiber (B), a non-woven fabric is produced by a thermal bond method of joining the fibers to each other by heat. In this case, a wet method or a dry method may be used. Further, also for a thermal bond fiber consisting of a core-shell type composite spin with the resin of the fiber (A) as the core, and the resin of the fiber (B) as the shell, the same effect can be exerted.

Specifically, using the thermal bond method, it is possible to mention as an example a non-woven fabric consisting of two or more different types of thermoplastic fibers having differing heat resistances such as glass transition points or melting points or the like, joined by thermal fusion between one fiber having a high heat resistance, another fiber having a low heat resistance. In this case, the joining can be obtained by thermal bonding at a temperature where the thermoplastic fiber having the lower heat resistance melts, but the fiber having the higher heat resistance does not melt. A non-woven fabric produced from two or more types of thermoplastic fibers with differing heat resistances can produce a thermal fusion non-woven fabric by adjusting the type of the thermoplastic fibers or the thermal fusion temperature.

The fiber (B) in the embodiment of the present invention comprises no less than 10 mass % of either of a cyclic olefin-based resin (B1) or a crystalline thermoplastic resin (B2), but it is preferable to comprise no less than 10 mass % of a cyclic olefin-based resin (B1). By using a composition comprising a cyclic olefin-based resin, it is possible to make a non-woven fabric having an extremely small rate of absorption with respect to volatile low molecular compounds from medicines.

The web of the fiber can be produced by a dry method randomly forming a thin sheet shape by utilizing an air flow or mechanically combing relatively short fibers on the order of 15 mm to 100 mm, or a wet method of blending extremely short fibers on the order of 6 mm or less with water, and straining as for paper, or the like. From the point that the texture is good and the surface smoothness is excellent, it is preferable to use the wet method. Further, without being limited to a web consisting of short fibers such as those described above, a web of fibers consisting of long fibers on the order of 100 mm or more may also be used.

Among these, short fibers where the length of the fiber (A) and the fiber (B) are 0.2 mm to 10 mm are preferable. With short fibers, it is possible to obtain a smoother texture.

Below, one embodiment of the non-woven fabric of the present invention is explained. For example, using the non-woven fabric of the embodiment of the present invention as a non-woven fabric for a patch, it is possible to produce a substrates for a patch, or a patch or the like.

<Substrate for a Patch>

It is also possible to laminate the non-woven fabric of the embodiment of the present invention and a film, to produce a substrate for a patch. The film can be produced, for example, by forming a thermoplastic resin composition into a film shape by a previously known method. As the thermoplastic resin composition, a thermoplastic resin composition comprising a cyclic olefin-based resin composition may be used. By using a thermoplastic resin composition comprising a cyclic olefin-based resin composition as the thermoplastic resin composition, it is possible to make extremely small the rate of absorption with respect to volatile low molecular compounds of the substrate for a patch.

<Patch>

A patch using the substrate for a non-woven fabric patch of the present embodiment, for example, may be constituted by forming a medicine-comprising layer comprising a volatile low molecular compound with a molecular weight of 800 or less on a substrate for a patch comprising the non-woven fabric of the embodiment of the present invention. The medicine-comprising layer, without being particularly limited may be one previously used in a medicinal application, and a plaster agent (tape agent) or a poultice or the like may be used.

EXAMPLES

Below, the present invention is specifically explained by showing examples, but the present invention is not in any way limited by these examples.

<Used Materials>

Cyclic olefin-based resin 1: Product name "TOPAS 9506F-04" produced by TOPAS Advanced Polymers, glass transition point 64° C. Cyclic olefin-based resin 2: Product name "TOPAS 8007F-04" produced by TOPAS Advanced Polymers, glass transition point 78° C. Cyclic olefin-based resin 3: Product name "TOPAS 5013L-10" produced by TOPAS Advanced Polymers, glass transition point 134° C. Cyclic olefin-based resin 4: Product name "TOPAS 6013F-04" produced by TOPAS Advanced Polymers, glass transition point 138° C. Cyclic olefin-based resin 5: Product name "TOPAS 6015S-04" produced by TOPAS Advanced Polymers, glass transition point 158° C. Cyclic olefin-based resin 6: Product name "TOPAS 6017S-04" produced by TOPAS Advanced Polymers, glass transition point 178° C. Cyclic olefin-based resin 7: Product name "TOPAS 6013M-07" produced by TOPAS Advanced Polymers, glass transition point 142° C. Polypropylene: Product name "Novatec PP SA3A" produced by Japan Polypropylene Corporation, melting point 165° C. High density polyethylene (HDPE): Product name "Novatec HD HJ580N", produced by Japan Polypropylene Corporation, melting point 134° C.

<Production of the Non-Woven Fabric>

Examples 1 to 6

As the fiber for the non-woven fabric (thermal bond fiber), using the materials shown in Table 1, a 2dtex short cut fiber (short fiber) with a cut length of 5 mm was obtained by using a melt spinning apparatus consisting of an extruder, a nozzle, a winding system, and the like, a heating apparatus, and a drawing apparatus provided with a take-up roll, and carrying out the preparation of the fiber using a fiber cut machine. A short fiber (A) made of a cyclic olefin-based resin (A1) and a short fiber (B) made of a cyclic olefin-based resin (B1) were blended such that the mass ratio was 80:20, and the blended short fibers were blended with water, and were filtered as paper to form a sheet, and heat processing was carried out at 150° C. in a Yankee drier, and the fibers were melt bonded to each other at the short fibers made of the resin (B1), and a non-woven fabric with a mass per unit area of about 50 g/m² was obtained.

Example 7

The short fibers (A) made from the resin (A1) show in Table 1 and, a polypropylene-based (PP) core-shell type composite fiber as the short fiber (B) (core portion: polypropylene (PP)/shell portion: high density polyethylene (HDPE) (the mass ratio of the core portion and the shell portion is 50:50, therefore, in the fiber (B), HDPE was comprised at 50 mass % as a crystalline fiber thermoplastic resin (B2)), 2dtex, fiber length 5 mm) were blended in a ratio (A):(B) of 80:20, and the high density polyethylene of the shell (melting point 130° C.) was melted whereby the fibers were melt bonded and the non-woven fabrics of Examples 1 to 6 were obtained in the same way.

Comparative Examples 1 and 2

The fiber (A) made from the cyclic olefin-based resin (A1) shown in the table and the fiber (B) made from the cyclic olefin-based resin (B1) or the (B2) were blended in a fiber ratio of (A):(B)=80:20 in the same way as Examples 1 to 7, and thermal processing was carried out in a Yankee drier at 150° C. Because the glass transition temperature difference between the short fiber (A) made from the resin (A1) and the fiber (B) comprising the resin (B1) or the crystalline thermoplastic resin (B2) is small, the fiber (B) was not sufficiently softened, and the joining of the fibers was weak, and a serviceable non-woven fabric could not be obtained.

Further, the melt fiber spinning temperatures of the respective cyclic olefin-based resins of Examples 1 to 7, and Comparative Examples 1 and 2, were as follows.
Cyclic olefin-based resin 1: 200° C.
Cyclic olefin-based resin 2: 220° C.
Cyclic olefin-based resin 3: 280° C.
Cyclic olefin-based resin 4: 290° C.
Cyclic olefin-based resin 5: 300° C.
Cyclic olefin-based resin 6: 320° C.
Cyclic olefin-based resin 7: 290° C.

TABLE 1

| | fiber(A) | | fiber(B) | | difference in heat resistance (° C.) |
|---|---|---|---|---|---|
| | (A1) | Tg (° C.) | (B1) or (B2) | Tg or Mp (° C.) | |
| Example1 | cyclic olefin-based resin3 | 134 | cyclic olefin-based resin2 | 78 | 56 |
| Example2 | cyclic olefin-based resin3 | 134 | cyclic olefin-based resin1 | 64 | 70 |
| Example3 | cyclic olefin-based resin4 | 138 | cyclic olefin-based resin2 | 78 | 60 |
| Example4 | cyclic olefin-based resin4 | 138 | cyclic olefin-based resin1 | 64 | 74 |
| Example5 | cyclic olefin-based resin5 | 158 | cyclic olefin-based resin2 | 78 | 80 |
| Example6 | cyclic olefin-based resin6 | 178 | cyclic olefin-based resin2 | 78 | 100 |
| Example7 | cyclic olefin-based resin6 | 178 | PP-based core-shell fiber (shell: HDPE core: PP) | 130 | 48 |
| Comparative Example1 | cyclic olefin-based resin5 | 158 | cyclic olefin-based resin7 | 142 | 16 |
| Comparative Exainple2 | cyclic olefin-based resin6 | 178 | cyclic olefin-based resin5 | 158 | 20 |

(In the table, "Tg or Mp" indicates a glass transition point in the case that the resin is a cyclic olefin-based resin, or in the case of the fiber (B) of Example 7 (olefin-based core-shell composite fiber) indicates a melting point of the high density polyethylene (HDPE) resin (crystalline thermoplastic resin (B2) of the shell portion. In the table, the difference in heat resistance indicates the difference between the "Tg" of the cyclic olefin-based resin (A1) included in the fiber (A), and the "Tg or Mp" of the cyclic olefin-based resin (B1) or crystalline thermoplastic resin (B2) included in the fiber (B).)

The rate of absorption of volatile low molecular compounds was measured for each of the non-woven fabrics of the Examples and Comparative Examples. Specifically, 30 g of a volatile substance (as the volatile substance, dl-camphor (molecular weight: 152) and 1-menthol (molecular weight: 156) were used), and each of the non-woven fabrics (0.1 g) shown in Table 1 were placed in a desiccator, and after leaving for 2 weeks at room temperature, the amount of the volatile substance (d1-camphor, 1-menthol) absorbed in the resin was measured by a headspace GC method. The results are shown in Table 2.

TABLE 2

| non-woven fabric | d1-camphor | 1-menthol |
|---|---|---|
| Example1 | 1.9 microgram | 3.7 microgram |
| Example2 | 2.0 microgram | 3.6 microgram |

TABLE 2-continued

| non-woven fabric | dl-camphor | l-menthol |
|---|---|---|
| Example3 | 1.9 microgram | 3.6 microgram |
| Example4 | 1.9 microgram | 3.6 microgram |
| Example5 | 1.9 microgram | 3.7 microgram |
| Example6 | 1.9 microgram | 3.7 microgram |
| Example7 | 102 microgram | 80 microgram |
| Comparative Example1 | measurement not possible, could not obtain non-woven fabric | measurement not possible, could not obtain non-woven fabric |
| Comparative Example2 | measurement not possible, could not obtain non-woven fabric | measurement not possible, could not obtain non-woven fabric |

From Table 2, it can be understood that the non-woven fabrics of the present invention have a small rate of absorptivity of the volatile substance compared to the non-woven fabrics produced with polyethylene terephthalate. From these experimental results, it can be understood that the cyclic olefin-based resin-containing thermal bond non-woven fabric of the present invention produced from fibers including a cyclic olefin-based resin has a small rate of absorption of volatile low molecular compounds.

[Feel Tests]

Tests were carried out to confirm the feel in relation to the adhesion sensation of the non-woven fabric of the present invention. Specifically, tests (sensory evaluations) were carried out to confirm the feel of the non-woven fabrics disclosed in Table 2. Further, a polyester-based wet process non-woven fabric (mass per unit area 50 g/m²) was set as Comparative Example 3.

(Basis of Evaluation)

A: supple and soft feel
B: a somewhat soft feel
C: a hard and starchy feel

TABLE 3

| non-woven fabric | feel |
|---|---|
| Example1 | A |
| Example2 | A |
| Example3 | A |
| Example4 | A |
| Example5 | A |
| Example6 | A |
| Example7 | A |
| Comparative Example1 | measurement not possible, could not obtain non-woven fabric |
| Comparative Example2 | measurement not possible, could not obtain non-woven fabric |
| Comparative Example3 | B-C |

From Table 3, it can be understood that a patch produced using the non-woven fabric of the present invention is a patch excelling in feel compared with the polyester-based wet process non-woven fabric according to Comparative Example 3.

The invention claimed is:

1. A cyclic olefin-based resin-containing thermal bond non-woven fabric comprising at least a fiber (A) comprising no less than 50 mass % of a cyclic olefin-based resin (A1) having a glass transition point $Tg_{A1}$° C.,
   a fiber (B) comprising no less than 10 mass % of a cyclic olefin-based resin (B1) having a glass transition point $Tg_{B1}$° C., or a crystalline thermoplastic resin (B2) having a melting point $Mp_{B2}$° C., wherein
   fibers of the fiber (A) are not thermally fused and fibers of the fiber (B) are thermally fused,
   the $Tg_{A1}$ and the $Tg_{B1}$ are each 50° C. or more and 190° C. or less,
   $Tg_{A1} > Tg_{B1}$, or $Tg_{A1} > Mp_{B2}$,
   wherein the $Tg_{A1}$, the $Tg_{B1}$, the $Tg_{A1}$ and the $Mp_{B2}$ are measured by the DSC method disclosed in JIS K7121 under conditions of a temperature increase rate of 10° C./min, and
   a difference between the glass transition point $Tg_{A1}$° C. and the glass transition point $Tg_{B1}$° C., or the difference between the glass transition point $Tg_{A1}$° C. and the melting point $Mp_{B2}$° C. exceeds 20° C.

2. The cyclic olefin-based resin-containing thermal bond non-woven fabric according to claim 1, wherein the fiber (B) comprises no less than 10 mass % of the cyclic olefin-based resin (B1) having a glass transition point $Tb_{B1}$° C.

3. The cyclic olefin-based resin-containing thermal bond non-woven fabric according to claim 1, wherein the fiber (A) and the fiber (B) are short fibers having a length of 0.2 mm to 10 mm.

4. The cyclic olefin-based resin-containing thermal bond non-woven fabric according to claim 1, formed by a wet method.

5. The cyclic olefin-based resin-containing thermal bond non-woven fabric according to claim 1, wherein the cyclic olefin-based resin-containing thermal bond non-woven fabric is a substrate of a patch.

6. The cyclic olefin-based resin-containing thermal bond non-woven fabric according to claim 1, wherein the cyclic olefin-based resin (A1) and the cyclic olefin-based resin (B1) are copolymers of ethylene and norbornene.

\* \* \* \* \*